United States Patent [19]

Link

[11] Patent Number: 4,808,727

[45] Date of Patent: Feb. 28, 1989

[54] IMIDAZOLIUM HYDROGEN CARBONATES

[75] Inventor: Helmut Link, Basel, Switzerland

[73] Assignee: Hoffmann-LaRoche Inc., Nutley, N.J.

[21] Appl. No.: 102,067

[22] Filed: Sep. 29, 1987

[30] Foreign Application Priority Data

Oct. 3, 1986 [CH] Switzerland .................. 3955/86

[51] Int. Cl.⁴ ............... C07D 233/66; C07D 233/04; C07D 413/00; C07D 403/00

[52] U.S. Cl. ........................... 548/337; 548/354; 544/139; 544/370; 544/129; 544/130; 544/82; 544/121; 544/364; 544/60; 546/210; 546/187

[58] Field of Search ............... 548/337, 354; 544/139, 544/370, 129, 130, 82, 121, 364, 60; 546/210, 187

[56] References Cited

U.S. PATENT DOCUMENTS

| | | | |
|---|---|---|---|
| 3,050,520 | 8/1962 | Erner et al. | 548/337 |
| 3,577,553 | 5/1971 | Feriauto | 548/337 |
| 4,025,607 | 5/1977 | Stähle et al. | 548/337 |

FOREIGN PATENT DOCUMENTS

| | | | |
|---|---|---|---|
| 2127355 | 6/1971 | Fed. Rep. of Germany | 548/337 |
| 146595 | 10/1979 | Fed. Rep. of Germany | 548/337 |
| 2196157 | 3/1974 | France | 548/337 |

OTHER PUBLICATIONS

Bull. Chem. Soc. of Japan 51, 1846–1855 (1978).
Chem. Ber. 100, 3418–3426 (1967).
Chemical Abstracts 102, 59125x (1985).
Tetrahedron Letters 1978, 1295–1298.
Karpitschka, Eva Marie; Elektrophile N-Aminierung von Dimethylxanthinen and Einfachen Imidazolen. Funktionelle Derivate der N-Aminoverlindungen. Innsbruck 1981, Universitat, Dissertation.
Mussner, Renate; Ueber N-Aminoderivate von 2-Methylimidazolene. Innsbruck 1982, Universitat, Diplomarbeit.
Synthesis 1982, 592–594.
Chem. Pharm. Bull., 22, 482–484 (1974).
Chemical Abstracts 101, 2110040e (1984).

Primary Examiner—Mary C. Lee
Assistant Examiner—Robert C. Whittenbaugh
Attorney, Agent, or Firm—Jon S. Saxe; Bernard S. Leon; William G. Isgro

[57] ABSTRACT

The pharmaceutically acceptable salts corresponding to the imidazolium hydrogen carbonates of the formula

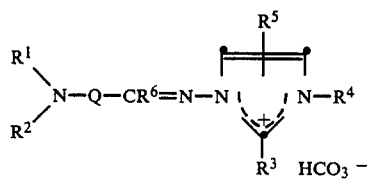

wherein the symbol Q is arylene or heteroarylene, the group $-NR^1R^2$ is a basic amino group, $R^3$ is hydrogen, lower alkyl, lower hydroxyalkyl, lower alkoxyalkyl, lower haloalkyl, lower alkylthio, lower alkoxy or the group $-(A)_n-Ra$, $R^4$ is a saturated or partially unsaturated lower hydrocarbon group, a basic amino group or the group $-N=CRc-Rb$, $-CHRcRd$, $-N-H-CHRcRd$, $-NH-CO-Re$ or $-CH-Rc-CO-Re$, $R^5$ is hydrogen, lower alkyl, lower hydroxyalkyl, lower alkoxyalkyl, lower haloalkyl, aryl or a fused benzene ring, $R^6$ is hydrogen or lower alkyl, Ra and Rb each is aryl, heteroaryl or a basic amino group, Rc is hydrogen or lower alkyl, Rd is aryl or heteroaryl, Re is hydrogen, a saturated or partially unsaturated lower hydrocarbon group optionally attached via an oxygen atom or an aryl, heteroaryl or basic amino group optionally attached via a lower alkyl group, A is vinylene or lower alkylene, n is the integer 0 or 1 and the dotted line is an additional double bond, possess valuable antibacterial, antimycotic, protozoocidal and/or anthelmintic properties. The imidazolium bicarbonates of formula I can be used to prepare such pharmaceutically acceptable, especially water-soluble, salts in a simple and inexpensive manner.

29 Claims, No Drawings

IMIDAZOLIUM HYDROGEN CARBONATES

BRIEF DESCRIPTION OF THE INVENTION

The invention relates to imidazolium hydrogen carbonates of the formula

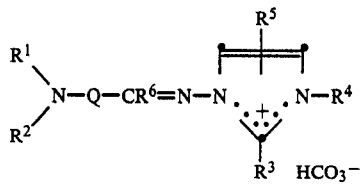

wherein the symbol Q is arylene or heteroarylene, the group —NR$^1$R$^2$ is a basic amino group, R$^3$ is hydrogen, lower alkyl, lower hydroxyalkyl, lower alkoxyalkyl, lower haloalkyl, lower alkylthio, lower alkoxy or the group —(A)$_n$—Ra, R$^4$ is a saturated or partially unsaturated lower hydrocarbon group, a basic amino group or the group —N=CRc—Rb, —CHRcRd, —N-H—CHRcRd, —NH—CO—Re or —CH-Rc—CO—Re, R$^5$ is hydrogen, lower alkyl, lower hydroxyalkyl, lower alkoxyalkyl, lower haloalkyl, aryl or a fused benzene ring, R$^6$ is hydrogen or lower alkyl, Ra and Rb each is aryl, heteroaryl or a basic amino group, Rc is hydrogen or lower alkyl, Rd is aryl or heteroaryl, Re is hydrogen, a saturated or partially unsaturated lower hydrocarbon group optionally attached via an oxygen atom or an aryl, heteroaryl or basic amino group optionally attached via a lower alkyl group, A is vinylene or lower alkylene, n is the integer 0 or 1 and the dotted line is an additional double bond.

The pharmaceutically acceptable salts corresponding to the compounds of formula I possess valuable pharmacological properties. In particular, these pharmaceutically acceptable salts possess antibacterial, antimycotic, protozoocidal and/or anthelmintic properties. The compounds of formula I can be used to prepare such pharmaceutically acceptable, especially water-soluble, salts in a simple and inexpensive manner.

DETAILED DESCRIPTION OF THE INVENTION

The invention relates to imidazolium hydrogen carbonates of the formula

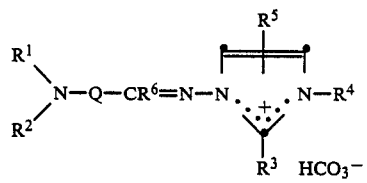

wherein the symbol Q is arylene or heteroarylene, the group —NR$^1$R$^2$ is a basic amino group, R$^3$ is hydrogen, lower alkyl, lower hydroxyalkyl, lower alkoxyalkyl, lower haloalkyl, lower alkylthio, lower alkoxy or the group —(A)$_n$—Ra, R$^4$ is a saturated or partially unsaturated lower hydrocarbon group, a basic amino group or the group —N=CRc—Rb, —CHRcRd, —N-H—CHRcRd, —NH—CO—Re or —CH-Rc—CO—Re, R$^5$ is hydrogen, lower alkyl, lower hydroxyalkyl, lower alkoxyalkyl, lower haloalkyl, aryl or a fused benzene ring, R$^6$ is hydrogen or lower alkyl, Ra and Rb each is aryl, heteroaryl or a basic amino group, Rc is hydrogen or lower alkyl, Rd is aryl or heteroaryl, Re is hydrogen, a saturated or partially unsaturated lower hydrocarbon group optionally attached via an oxygen atom or an aryl, heteroaryl or basic amino group optionally attached via a lower alkyl group, A is vinylene or lower alkylene, n is the integer 0 or 1 and the dotted line is an additional double bond.

The pharmaceutically acceptable salts corresponding to the compounds of formula I possess valuable pharmacological properties. In particular, these pharmaceutically acceptable salts possess antibacterial, antimycotic, protozoocidal and/or anthelmintic properties. The above compounds of formula I can be used to prepare such pharmaceutically acceptable, especially water-soluble, salts in a simple and inexpensive manner.

Objects of the present invention are the compounds of formula I, a process for the preparation thereof, a process for the preparation of the pharmaceutically acceptable salts corresponding to the compounds of formula I, as well as the use of the compounds of formula I for the preparation of the pharmaceutically acceptable salts corresponding thereto.

The term "lower" denotes residues and compounds with a maximum of 7, preferably a maximum of 4, arbon atoms. The term "alkyl", taken alone or in combinations such as "alkyl groups", "alkoxy" and "alkylthio", denotes straight-chain or branched, saturated hydrocarbon residues such as methyl, ethyl, n-propyl, i-propyl, n-butyl, s-butyl, i-butyl, t-butyl and the like.

The term "saturated or partially unsaturated hydrocarbon group" denotes open-chain and cyclic groups and combinations thereof. Examples of saturated and partially unsaturated lower hydrocarbon groups are: lower alkyl groups such as methyl, ethyl, propyl, i-propyl, s-butyl and i-butyl; lower alkenyl groups such as 2-propenyl, 2-butenyl, 3-butenyl and 2-methyl-2-propenyl; lower cyclo-alkyl groups optionally substituted by lower alkyl groups such as cyclopropyl, cyclopentyl, 2-methylcyclopentyl, cyclohexyl and 3-methylcyclohexyl; lower cycloalkenyl groups optionally substituted by lower alkyl groups such as 3-cyclopentenyl, 1-methyl-3-cyclopentenyl and 3-cyclo-hexenyl; lower alkyl or alkenyl groups substituted by lower cycloalkyl or cycloalkenyl groups such as cyclopropylmethyl, cyclopropylethyl, cyclopentylmethyl, cyclohexylmethyl, 2-cyclohexenyl-methyl and 3-cyclopropyl-2propenyl. The preferred lower hydrocarbon groups are saturated. The lower alkyl and lower cycloalkyl groups, especially the lower alkyl groups, are particularly preferred lower hydrocarbon groups.

The term "aryl" denotes carbocyclic aromatic groups, preferably mono- or bicyclic groups, i.e. phenyl and naphthyl groups, especially phenyl groups. These groups are optionally substituted by one, two or three substituents from the group consisting of basic amino, lower alkyl, lower alkoxy, lower alkylthio, lower alkanoyl, lower alkoxycarbonyl, aryl (especially phenyl), halogen, trifluoromethyl, hydroxy, nitro and cyano. These groups are preferably unsubstituted or substituted by one, two or three substituents from the group consisting of lower alkyl, lower alkoxy, lower alkylthio, halogen, nitro and di(lower alkyl)amino.

The term "arylene" denotes carbocyclic aromatic groups with two free valencies, preferably mono- or bicyclic groups, i.e. phenylene and naphthylene groups, especially 1,4- or 1,2-phenylene groups and, in particular, 1,4-phenylene groups. These groups can be substituted by one or two substituents from the group consisting of lower alkyl, lower alkoxy, lower alkylthio, lower alkanoyl, lower alkoxycarbonyl, aryl (especially phenyl), halogen, trifluoromethyl, hydroxy, nitro and cyano. They are preferably unsubstituted.

The term "heteroaryl" denotes heterocyclic aromatic groups, preferably mono- or bicyclic groups, especially 5- or 6-membered aromatic heterocycles which are optionally fused with a benzene ring and which can be optionally substituted by one, two or three substituents from the group consisting of basic amino, lower alkyl, lower alkoxy, lower alkylthio, lower alkanoyl, lower alkoxycarbonyl, aryl (especially phenyl), halogen, trifluoromethyl, hydroxy, nitro and cyano. The 5-membered aromatic heterocycles preferably contain as the hetero ring member(s) an oxygen or sulfur atom or an imino group and optionally in addition one or two nitrogen atoms. The 6-membered aromatic heterocyles preferably contain as the ring member(s) one, two or three nitrogen atoms.

The term "heteroarylene" denotes heterocyclic aromatic groups with two free valencies, preferably mono- or bicyclic groups, especially 5- and 6-membered aromatic heterocycles with two free valencies, which are optionally fused with a benzene ring and which can be substituted by one or two substituents from the group consisting of lower alkyl, lower alkoxy, lower alkylthio, lower alkanoyl, lower alkoxycarbonyl, aryl (especially phenyl), halogen, trifluoromethyl, hydroxy, nitro and cyano.

The term "halogen" denotes the four forms fluorine, chlorine, bromine and iodine.

The term "basic amino group" or "basic amino" denotes unsubstituted or mono- or disubstituted amino groups with basic character. The basic amino groups can be represented by the formula —NRR'. Therein, preferably R is hydrogen or lower alkyl and R' is hydrogen or a saturated or partially unsaturated lower hydrocarbon group which is optionally substituted by one or two lower alkoxy or hydroxy groups or by an amino, lower alkylamino, lower dialkylamino, oxo, lower alkoxycarbonyl or lower alkylenedioxy group or R and R' together with the nitrogen atom are a 4- to 7-membered saturated N-heterocycle which is optionally substituted by one or two lower alkyl groups and which can contain as a ring member in place of a methylene group an oxygen or sulfur atom or the group >SO, >SO$_2$, >CO, >CH-Rf or >N-Rg in which Rf is hydroxy, lower alkanoyl, lower alkoxycarbonyl, carbamoyl, mono- or di(lower alkyl)carbamoyl or a saturated or partially unsaturated lower hydrocarbon group which is optionally attached via an oxygen atom and which is optionally substituted by one or two lower alkoxy or hydroxy groups or by an amino, lower alkylamino, lower dialkylamino, oxo, lower alkoxycarbonyl or lower alkylenedioxy group and Rg is hydrogen, lower alkanoyl, lower alkoxycarbonyl, carbamoyl, mono- or di(lower alkyl)-carbamoyl or a saturated or partially unsaturated lower hydrocarbon group which is optionally substituted by one or two lower alkoxy or hydroxy groups or by an amino, lower alkylamino, lower dialkylamino, oxo, lower alkoxycarbonyl or lower alkylenedioxy group.

Especially preferred basic amino groups —NRR' are those in which R is hydrogen or lower alkyl and R' is a saturated lower hydrocarbon group or R and R' together with the nitrogen atom are a 4-, 5- or 6-membered saturated N-heterocycle which is optionally substituted by a hydroxy, lower alkoxy, lower hydroxyalkyl or lower alkoxyalkyl group or a 6-membered saturated N-heterocycle which is optionally substituted by one or two lower alkyl groups and which contains in place of a methylene group an oxygen or sulfur atom or an imino or lower alkylimino group.

Particularly preferred basic amino groups —NRR' are those in which R and R' each are lower alkyl or together with the nitrogen atom are 1-pyrrolidinyl, 1-piperidinyl, 4morpholinyl, 2,6-dimethyl-4-morpholinyl, 4-thiomorpholinyl or 4-methyl-1-piperazinyl.

If a compound of formula I contains more than one basic amino group, then these can be the same or different.

The term "leaving group" preferably denotes halogen atoms such as chlorine, bromine and iodine, lower alkylsulfonyloxy groups such as methylsulfonyloxy and arylsulfonyloxy groups such as p-tolylsulfonyloxy.

In a special embodiment the present invention is concerned with compounds of formula I above in which $R^3$ is lower alkyl.

In a further special embodiment, the invention is concerned with compounds of formula I above in which $R^3$ is the group —(A)$_n$—Ra. Preferably, either n is the number 0 and Ra is an unsubstituted phenyl group or a phenyl group substituted by one, two or three substituents from the group consisting of lower alkyl, lower alkoxy, lower alkylthio, halogen, nitro and di(-lower alkyl)amino, whereby Ra is, in particular, an unsubstituted phenyl group or phenyl groups monosubstituted by lower alkyl, lower alkoxy or halogen, such as phenyl, p-chlorophenyl, p-tolyl and m-methoxyphenyl, or n is the number 1, A is vinylene and Ra is the group —NRR' in which R and R' each are hydrogen or lower alkyl or together with the nitrogen atom are a 5- or 6-membered saturated heterocycle which is optionally substituted by one or two lower alkyl groups and which contains as the hetero atom(s) one or two nitrogen atoms or one nitrogen atom and one oxygen or sulfur atom, and R and R' in this case each preferably are lower alkyl, especially methyl, or together with the nitrogen atom signify 4-morpholinyl or 1-piperidinyl.

The symbol $R^5$ preferably is hydrogen.

In a preferred embodiment $R^4$ is the group —N=C-$R^6$—Q—NR$^1$R$^2$.

In a further preferred embodiment, $R^4$ is the group —N=CRc—Rb in which Rc preferably is hydrogen and Rb preferably is an unsubstituted phenyl group or a phenyl group substituted by one, two or three substituents from the group consisting of lower alkyl, lower alkoxy, lower alkylthio, halogen and nitro. Quite particularly, Rb is p-nitrophenyl.

The symbol Q preferably is 1,4-phenylene optionally substituted by one or two substituents from the group consisting of lower alkyl and lower alkoxy. In an especially preferred embodiment, the symbol Q is 1,4-phenylene.

$R^1$ and $R^2$ each preferably are lower alkyl. In an especially preferred embodiment $R^1$ and $R^2$ each are methyl.

The symbol $R^6$ preferably is hydrogen.

The imidazolium salts listed hereinafter are preferred representative of the class of substance described by formula I:

1,3-Bis[[p-(dimethylamino)benzylidene]amino]-2-[2-(dimethylamino)vinyl]imidazolium hydrogen carbonate, 1,3-bis[[p-(dimethylamino)benzylidene]amino]-2-isopropylimidazolium hydrogen carbonate,
1,3-bis[[p-(dimethylamino)benzylidene]amino]-2-methylimidazolium hydrogen carbonate and
1,3-bis[[p-(dimethylamino)benzylidene]amino]-2-phenylimidazolium hydrogen carbonate.

The compound of formula I can be prepared in accordance with the invention by treating a compound of the formula

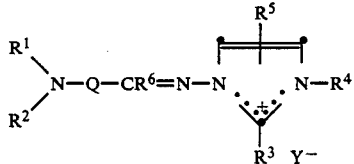

II where $R^1$, $R^2$, $R^3$, $R^4$, $R^5$, $R^6$, Q and the dotted line have the above significance and $Y^-$ is an anion, with a concentrated, aqueous alkali metal hydrogen carbonate solution.

A saturated hydrogen carbonate solution is preferably used. Sodium is the preferred alkali metal. The process in accordance with the invention can also be carried out in the presence of an organic solvent, whereby solvents which are not miscible with water, for example, halogenated hydrocarbons such as chloroform, especially come into consideration. $Y^-$ is preferably a halide, especially a chloride, bromide or iodide. The reaction is preferably carried out at room temperature.

The imidazolium hydrogen carbonates in accordance with the invention are practically insoluble in the reaction medium and can be isolated by filtration.

As mentioned earlier, the imidazolium hydrogen carbonates can be used to prepare corresponding pharmaceutically acceptable, and especially water-soluble, salts in a simple and inexpensive manner. The conversion of the imidazolium hydrogen carbonates into the corresponding pharmaceutically acceptable salts of the formula

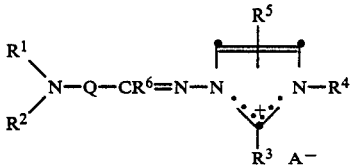

III wherein $R^1$, $R^2$, $R^3$, $R^4$, $R^5$, $R^6$, Q and the dotted line have the above significance and $A^-$ is a pharmaceutically acceptable anion, can be carried out by treating the imidazolium hydrogen carbonates with the acid corresponding to the desired pharmaceutically acceptable anion. Water and lower alcohols such as methanol or mixtures thereof are preferably used as the solvent. The reaction is preferably carried out at room temperature.

Suitable acids corresponding to the pharmaceutically acceptable anions are, for example, acetic acid, benzenesulfonic acid, benzoic acid, tartaric acid, hydrogen bromide, hydrogen chloride, citric acid, fumaric acid, malic acid, maleic acid, mandelic acid, methanesulfonic acid, phosphoric acid, succinic acid, sulfuric acid and p-toluenesulfonic acid.

Due to the fact that as the reaction product, in addition to the desired salt and water, there results carbon dioxide, which is released continuously, there is no need to use the above acids in large excess. Depending on the strength of the acid, no excess is generally required.

The compounds of formula II can be prepared by (a) reacting a compound of the formula

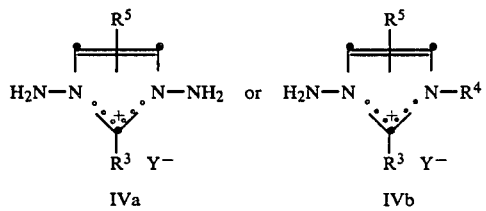

IVa    IVb wherein $R^3$, $R^4$, $R^5$, the dotted line and $Y^-$ have the above significance, with a carbonyl compound of the formula $$R^1R^2N-Q-CO-R^6 \qquad V$$

wherein $R^1$, $R^2$, $R^6$ and Q have the above significance, or (b) reacting a compound of the formula

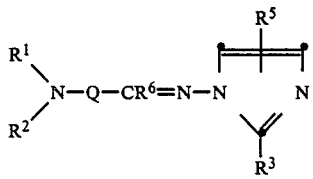

VI wherein $R^1$, $R^2$, $R^3$, $R^5$, $R^6$ and Q have the above significance with a compound of the formula $$R^{41}-X \qquad VII$$

wherein $R^{41}$ is a saturated or partially unsaturated lower hydrocarbon group or the group —CHRcRd or —CHRc—CO—Re and X is a leaving group, and Rc, Rd and Re have the above significance, or (c) condensing a compound of the formula

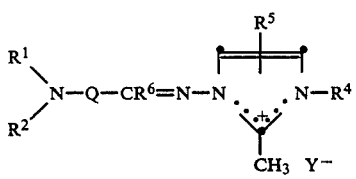

IIa wherein $R^1$, $R^2$, $R^4$, $R^5$, $R^6$, Q, $Y^-$ and the dotted line have the above significance, with an aldehyde of the formula $$Ra-CHO \qquad VIII$$

wherein Ra has the above significance, or (d) reacting a compound of the formula

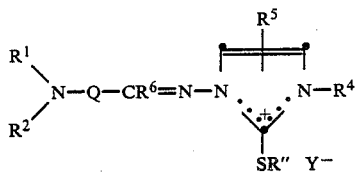

$$\text{IIb}$$

wherein $R^1$, $R^2$, $R^4$, $R^5$, $R^6$, Q, $Y^-$ and the dotted line have the above significance and R" is lower alkyl, with ammonia or a primary or secondary basic amine.

In several of the above processes (a)-(d), it is necessary to block by protecting groups any reactive amino and/or hydroxyl groups in the starting materials. These cases are readily recognizable by the person of ordinary skill in the art and the choice of the respective suitable protecting groups also presents no problems to one skilled in the art.

The reaction of amines with aldehydes or ketones in accordance with process variant (a) is a reaction which is known and which is faimilar to any person of ordinary skill in the art. Suitable solvents are, for example, water, lower fatty acids such as acetic acid and propionic acid, lower alcohols such as methanol, ethanol, 1-propanol and 2-propanol, lower fatty acid esters such as ethyl acetate, lower ethers such as diethyl ether, t-butyl methyl ether, ethylene glycol dimethyl ether, tetrahydrofuran and dioxane, halogenated lower hydrocarbons such as methylene chloride, chloroform and ethylene chloride, aromatic hydrocarbons such as benzene, toluene and xylene, acetonitrile, N,N-dimethylformamide and dimethyl sulfoxide. The reaction temperature is not critical. The reaction can be carried out, for example, in a range of about 0° C. up to the boiling temperature of the chosen solvent. However, the reaction is preferably carried out at room temperature. In the reaction with the less reactive ketones of formula V ($R^6$=lower alkyl) a condensation agent such as triethyloxonium tetrafluoroborate is preferably used.

Compounds of formula II in which $R^4$ is a saturated or partially unsaturated lower hydrocarbon group or the group —CHRcRd or —CHRc—CO—Re can be prepared in accordance with process variant (b) by alkylating imidazole derivatives of formula VI. This is also a reaction which is known per se and which is familiar to any person of ordinary skill in the art. Suitable solvents are, for example, halogenated lower hydrocarbons such as methylene chloride, chloroform and ethylene chloride, open-chain or cyclic ethers such as diethyl ether, t-butyl methyl ether, ethylene glycol dimethyl ether, tetrahydrofuran and dioxane, lower fatty acid esters such as ethyl acetate, lower alcohols such as methanol, ethanol, 1-propanol and 2-propanol, aromatic hydrocarbons such as benzene, toluene and xylene, acetonitrile, N,N-dimethylformamide and dimethyl sulfoxide. A lower alcohol such as 2-propanol or acetonitrile is preferably used. The reaction temperature is not critical. For example, the reaction can be carried out in a range of about 0° C. up to the boiling temperature of the solvent, preferably in a range of about room temperature to about 60° C.

Compounds of formula II in which $R^3$ is the group —CH=CH—Ra can be prepared in accordance with process variant (c) by condensing a compound of formula IIa with an aldehyde or formula VIII. Also, in this case, the reaction is known and is familiar to any person or ordinary skill in the art. Insofar as Ra is aryl or heteroaryl, the reaction is preferably carried out in the presence of a secondary amine, especially a cyclic amine such as piperidine or morpholine. Suitable solvents are, for example, lower alcohols such as methanol, ethanol, 1-propanol and 2-propanol, aromatic hydrocarbons such as benzene and toluene, open-chain and cyclic ethers such as ethylene glycol dimethyl ether, tetrahydrofuran and dioxan, halogenated lower hydrocarbons such as methylene chloride, N,N-dimethylformamide and dimethyl sulfoxide. The reaction is preferably carried out at the boiling temperature of the chosen solvent. In a preferred embodiment, there is used as the solvent an entrainer, for example, an aromatic hydrocarbon or a halogenated lower hydrocarbon, and the reaction water which is formed is removed with a water separator.

Insofar as Ra is a basic amino group, the aldehyde or formula VIII is preferably used in the form of a corresponding di(lower akyl)acetal, whereby the previously mentioned solvents are also suitable for the present case. A lower alcohol such as 1-propanol, a halogenated lower hydrocarbon such as methylene chloride or dimethylformamide is preferably used as the solvent. The reaction temperature is not critical. The reaction can be carried out in a range of about room temperature up to the boiling temperature of the chosen solvent. However, the reaction is preferably carried out in a range of about room temperature up to about 100° C.

Compounds of formula II in which $R^3$ is a basic amino group can be prepared in accordance with process variant (d) by reacting a compound of formula IIb with ammonia or a primary or secondary basic amine. Also, in this case, the reaction is known and is familiar to any person or ordinary skill in the art. Suitable solvents are, for example, halogenated lower hydrocarbons such as methylene chloride, open-chain and cyclic ethers such as diethyl ether, t-butyl methyl ether, tetrahydrofuran and dioxane, N,N-dimethylformamide, acetonitrile and dimethyl sulfoxide, N,N-Dimethylformamide and acetonitrile are preferred solvents. The reaction temperature is not critical and the reaction can be carried out, for example, in a range of about 0° C. up to the boiling temperature of the chosen solvent. However, the reaction is preferably carried out at room temperature.

The compounds of formula IVa used as starting materials can be prepared, for example, in accordance with the following Reaction Scheme I in which $R^3$, $R^5$, $Y^-$ and the dotted line have the above significance:

Reaction Scheme 1

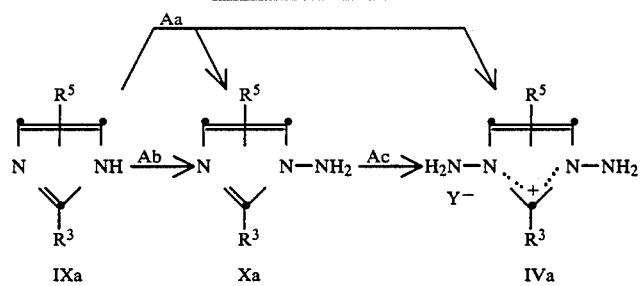

Compounds of formula IVa in which $R^3$ is lower alkylthio can also be prepared, for example, in accordance with the following Reaction Scheme II in which $F^5$, $R''$, $Y^-$ and the dotted line have the above significance and $\phi$ is phenyl:

Compounds of formula IVa in which $R^3$ is the group —CH=CH—Ra can also be prepared, for example, in accordance with the following Reaction Scheme III in which $R^5$, Ra, $Y^-$, the dotted line and $\phi$ have the above significance:

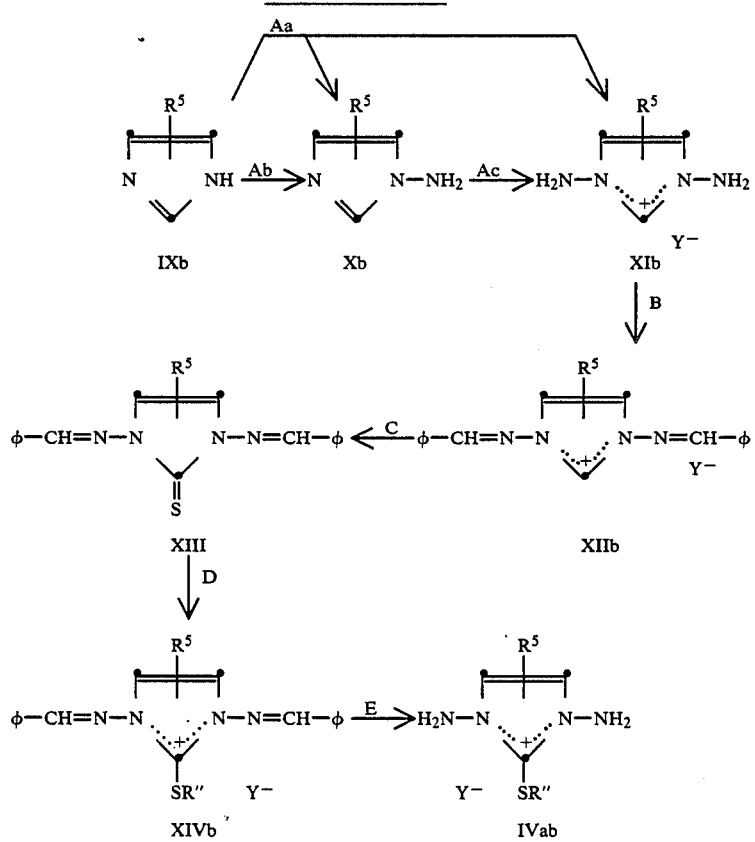

Reaction Scheme III

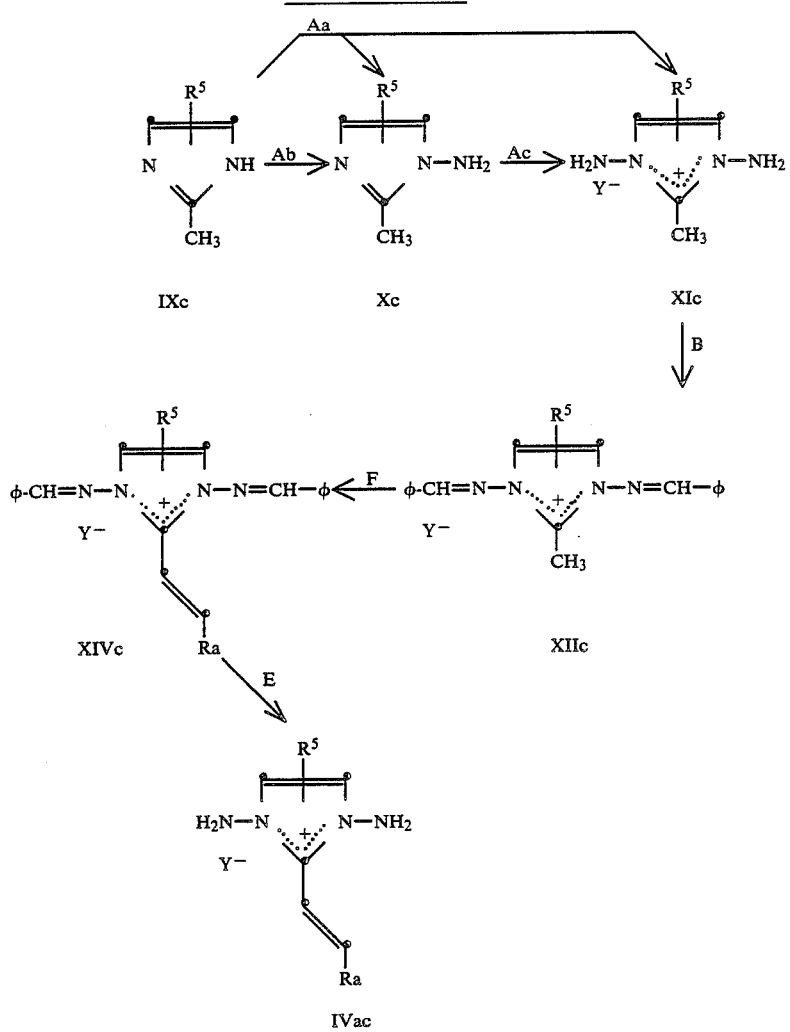

Compounds of formula IVa in which $R^3$ is a basic amino group can also be prepared, for example, in accordance with the following Reaction Scheme IV in which $R^5$, $Y^-$, the dotted line and $\phi$ have the above significance and Ra" is a basic amino group:

Reaction Scheme IV

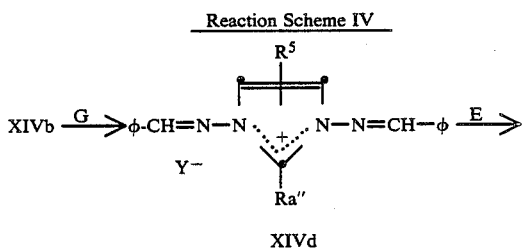

-continued
Reaction Scheme IV

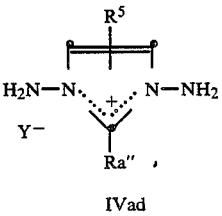

The compounds of formula IVa in which $R^3$ is the group —A'—Ra", A' is lower alkylene and Ra" is a basic amino group can also be prepared, for example, in accordance with the following Reaction Scheme V in which $R^5$, Ra", A', $\phi$, $Y^-$ and the dotted line have the above significance and X' is a halogen atom:

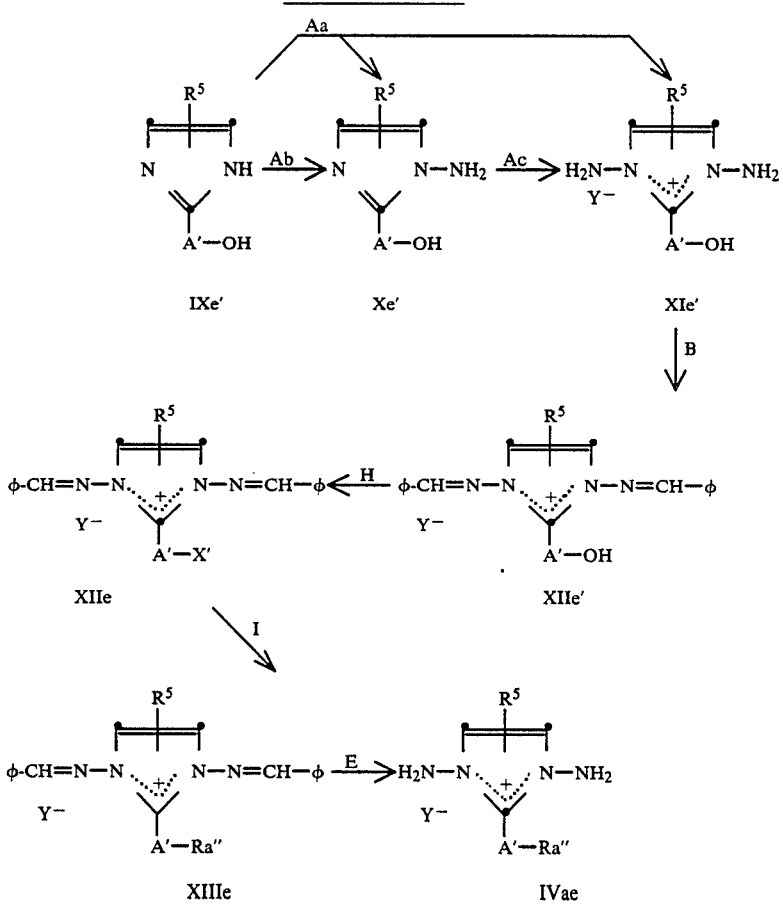

Reaction Scheme V

The compounds of formula IVb can be prepared in accordance with the foregoing Reaction Schemes I-V by in each case using as the starting material in place of a compound of the formula X a corresponding compound of the formula

XV wherein Rh is hydrogen, methyl, the group —A'—OH or $R^3$ and A', $R^3$, $R^4$ and $R^5$ have the above significance.

The compounds of formula IVb in which $R^4$ is a saturated or partially unsaturated lower hydrocarbon group or the group —CHRcRd or —CHRc—CO—Re can also be prepared, for example, in accordance with the following Reaction Scheme VI in which $R^3$, $R^{41}$, $R^5$, $Y^-$, $\phi$ and the dotted line have the above significance:

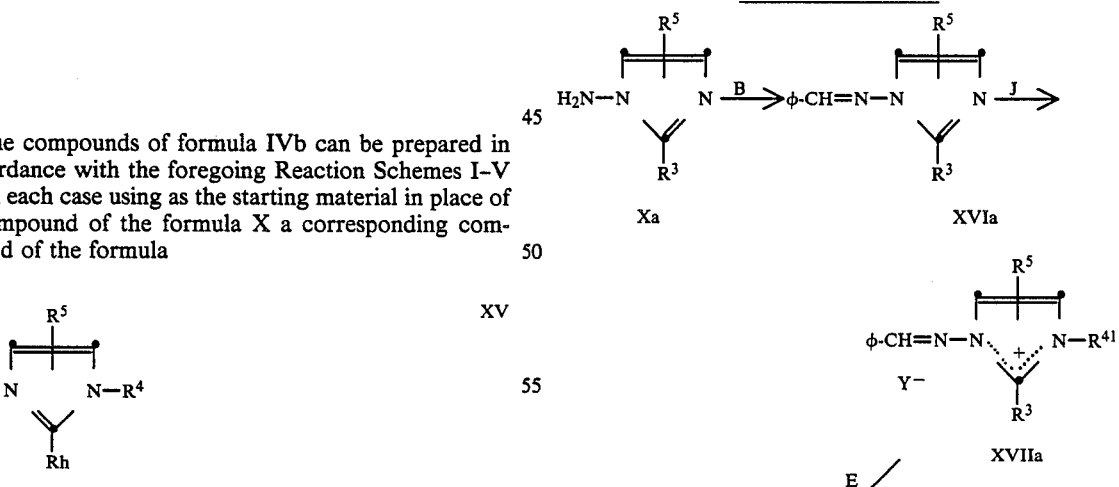

Reaction Scheme VI

The compounds of formula IVb in which $R^4$ is a saturated or partially unsaturated lower hydrocarbon group or the group —CHRcRd or —CHRc—CO—Re and $R^3$ is the group —SR", —CH=CH—Ra, Ra" or —A'—Ra" can also be prepared by converting a compound of formula Xb, Xc or Xe' in accordance with the foregoing Reaction Scheme VI in place of the compound Xa into the compound corresponding to formula XVIIa and further processing this in place of the compounds of formula XII in accordance with Reaction Schemes II, III, IV and V.

The reaction steps A–G referred to in the Reaction Schemes are explained hereinafter in more detail. In each case the reactions are known and are familiar to any person or ordinary skill in the art.

Aa: This reaction step is an electrophilic amination with an aminating agent such as O-(2,4-dinitrophenyl)-hydroxylamine, O-mesitylenesulfonylhydroxylamine or hydroxylamine O-sulfonic acid or its salts with inorganic bases. Preferably, the corresponding alkali metal salts of hydroxylamine O-sulfonic acid, for example the sodium salt, are used and the reaction is carried out in aqueous solution. In this case there is generally obtained a mixture consisting of the diamine of formula IVa or XI and the monoamine of formula X. The two compounds can be separated from each other according to methods which are known and familiar to any person of ordinary skill in the art. The Examples following below contain detailed information concerning the separation of the mixtures obtained.

Ab: This reaction step is an electrophilic amination with an aminating agent such as O-diphenylfosphinyl-hydroxylamine or O-mesitylenesulfonylhydroxylamine, whereby the starting material is converted with a strong base into an alkali metal salt prior to the reaction with the aminating agent. Suitable bases are, for example, lower alkali metal alkoxides such as sodium methoxide and sodium ethoxide and alkali metal hydrides such as sodium hydride. Suitable solvents are, for example, N-methylpyrrolidone, N,N-dimethylformamide, lower alcohols, ethers such as tetrahydrofuran, diethylene glycol dimethyl ether, diethylene glycol diethyl ether and diethylene glycol dibutyl ether. The reaction temperature preferably lies in a range of about 0° C. to 100° C., with the reaction being preferably carried out at room temperature.

Ac: This reaction step is an electrophilic amination with an aminating agent such as O-diphenylphosphinyl-hydroxylamine or O-mesitylenesulfonylhydroxylamine. Suitable solvents are, for example, halogenated lower hydrocarbons such as chloroform, methylene chloride and ethylene chloride, ethers such as diethyl ether and tetrahydrofuran, lower alcohols such as ethanol, acetonitrile, N,N-dimethylformamide, dimethyl sulfoxide and mixtures thereof. The reaction temperature lies in the range of about 0° C. up to the boiling temperature of the chosen solvent. The reaction is preferably carried out at room temperature.

B: In this reaction step the corresponding starting material is converted into the corresponding aldimine with benzaldehyde. Suitable solvents are, for example, lower fatty acids such as acetic acid and propionic acid, lower alcohols such as methanol, ethanol and 2-propanol, acidicaqueous media, halogenated lower hydrocarbons such as methylene chloride, chloroform and ethylene chloride, open-chain and cyclic ethers such as diethyl ether, diisopropyl ether, t-butyl methyl ether, ethylene glycol dimethyl ether, diethylene glycol diethyl ether, tetrahydrofuran and dioxane, acetonitrile, N,N-dimethylformamide and dimethyl sulfoxide. The reaction can be carried out at a temperature in the range of about 0° C. up to the boiling temperature of the chosen solvent. The reaction is preferably carried out at room temperature.

C: The desired thioxo group can be introduced, for example, by treating the starting material with elementary sulfur in the presence of a tertiary amine and in a suitable solvent, for example, in pyridine. The reaction can be carried out in a range of about room temperature up to the boiling temperature of the reaction mixture.

D: The desired alkylation can be carried out, for example, by treating the starting material with an alkylating agent such as a tri(lower alkyl)oxonium tetrafluoroborate, for example, with trimethyloxonium tetrafluoroborate. Suitable solvents are, for example, halogenated lower hydrocarbons such as methylene chloride. The reaction is preferably carried out at room temperature.

E: This reaction step is the hydrolysis of an aldimine. In a preferred embodiment, the corresponding starting material is treated with an aqueous acid and the aromatic aldehyde obtained is removed by steam distillation. Suitable acids are, for example, dilute hydrochloric acid and dilute hydrobromic acid and tetrafluoroboric acid.

F: In this reaction, a compound of formula XIIc is condensed with an aldehyde of formula VIII. When Ra is aryl or heteroaryl, the reaction is preferably carried out in the presence of a secondary amine, especially a cyclic amine such as piperidine or morpholine. Suitable solvents are, for example, lower alcohols such as methanol, ethanol, 1-propanol and 2-propanol, aromatic hydrocarbons such as benzene and toluene, open-chain and cyclic ethers such as ethylene glycol dimethyl ether, tetrahydrofuran and dioxane, halogenated lower hydrocarbons such as methylene chloride, N,N-dimethylformamide and dimethyl sulfoxide. The reaction is preferably carried out at the boiling temperature of the chosen solvent. In a preferred embodiment, there is used as the solvent an entrainer, for example, an aromatic hydrocarbon or a halogenated lower hydrocarbon, and the reaction water which is formed is removed with a water separator.

When Ra is a basic amino group, the aldehyde of formula VIII is preferably used in the form of a corresponding di(lower alkyl)acetal, whereby the previously mentioned solvents are also suitable in the present case. A lower alcohol such as 1-propanol, a halogenated lower hydrocarbon such as methylene chloride or dimethylformamide is preferably used as the solvent. The reaction temperature is not critical. The reaction can be carried out in a range of about room temperature up to the boiling temperature of the chosen solvent. However, the reaction is preferably carried out in a range of about room temperature up to about 100° C.

G: In this reaction, a compound of formula XIVb is reacted with ammonia or a primary or secondary basic amine. Suitable solvents are, for example, halogenated lower hydrocarbons such as methylene chloride, open-chain and cyclic ether such as diethyl ether, t-butyl methyl ether, tetrahydrofuran and dioxane, N,N-dimethylformamide, acetontrile and dimethyl sulfoxide. N,N-Dimethylformamide and acetonitrile are preferred solvents. The reaction temperature is not critical and the reaction can be carried out, for example, in a range of about 0° C. up to the boiling temperature of the chosen solvent. However, the reaction is preferably carried out at room temperature.

H: In this reaction, a compound of formula XIIe' is reacted with a halogenating agent such as thionyl chloride and phosphorus oxychloride, whereby excess halogenating agent is preferably used as the solvent. The reaction can be carried out at a temperature in the range of about 0° C. up to the boiling temperature of the reaction mixture.

I: In this reaction, a compound of formula XIIe is reacted with ammonia or a primary or secondary basic amine, whereby acetone or N,N-dimethylformamide is preferably used as the solvent. The reaction can be carried out at a temperature in the range of about room temperature up to the boiling temperature of the reaction mixture.

J: In this reaction step, the corresponding starting material is reacted with a compound of formula VI above. Suitable solvents are, for example, halogenated lower hydrocarbons such as methylene chloride, chloroform and ethylene chloride, open-chain and cyclic ethers such as diethyl ether, diisopropyl ether, ethylene glycol dimethyl ether, diethylene glycol diethyl ether, tetrahydrofuran and dioxane, acetonitrile and N,N-dimethylformamide. This reaction can be carried out at a temperature in the range of about 0° C. up to the boiling temperature of the chosen solvent.

The compounds of formula VI, which are used as starting materials, can be prepared in analogy to process variant (a) or to reaction step B described above by reacting a compound of formula Xa with an aldehyde or ketone of formula V.

As already mentioned earlier, the pharmaceutically acceptable salts corresponding to the compounds of formula I, that is, the compounds of formula III, possess valuable pharmacological properties. For example, they exhibit antiparasitic properties and are especially active against parasitic protozoa and worms. Their activity against parasitic worms, especially against nematodes such as filaria, is especially pronounced. These pharmacological properties can be determined by means of test methods which are known and which are familiar to any person of ordinary skill in the art.

The filaricidal activity of the compounds of formula III can be determined, for example, on cotton rats (Sigmodon hispidus) which have been infected with Litomosoides carinii. The infection with L. carinii is transmitted by the blood-sucking mite (Bdellonyssus bacoti) in which the development of the microfilaria to infectious larvae takes place. The cotton rats are infected by exposing them to bites of infected mites. Fourteen (14) weeks after the infection, groups of 2-4 animals are treated subcutaneously with the compound to be tested. Forty-two (42) days after treatment with the compound to be tested, the experimental animals are dissected, whereby the adult filaria are removed from the pleural cavity. Living and dead or encapsulated worms are separated from one another and weighed. The filaricidal activity is expressed as the percentage proportion of dead macrofilaria per treatment group. The $ED_{90}$ is then determined by means of Probit analysis using the values from different dosage groups. The $ED_{90}$ is that dosage at which 90% of the worms removed from the pleural cavity are dead. In the following Table, there are compiled the results which have been obtained in the previously described test with representative members of the class of compound defined by formula III. Moreover, the Table contains data concerning the acute toxicity of some of these compounds in mg/per kg in the case of single oral administration to mice.

TABLE

| Compound | $ED_{90}$ in mg/kg s.c. | $LD_{50}$ in mg/kg p.o. |
|---|---|---|
| A | 1.0 | 312-625 |
| B | 0.5 | — |
| C | 0.85 | — |
| D | <1.0 | 1250-2500 |

Compound A = 1,3-Bis[[p-(dimethylamino)benzylidene]amino]-2-[2-(dimethylamino)vinyl]imidazolium chloride.
Compound B = 1,3-Bis[[p-(dimethylamino)benzylidene]amino]-2-isopropylimidazolium chloride.
Compound C = 1,3-Bis[[p-(dimethylamino)benzylidene]amino]-2-methylimidazolium chloride.
Compound D = 1,3-Bis[[p-(dimethylamino)benzylidene]amino]-2-phenylimidazolium chloride.

The compounds of formula III can be used as medicaments, for example, in the form of pharmaceutical preparation for enteral or parenteral application. They can be administered, for example, perorally, in the form of tablets, coated tablets, dragees, hard and soft gelatine capsules, solutions, emulsions or suspensions, rectally, in the form of suppositories, or parenterally, in the form of injection solutions.

The preparation of the pharmaceutical preparations can be carried in a manner which is familiar to any person of ordinary skill in the art by bringing the described compounds of formula III, optionally in combination with other therapeutically valuable substances, into a galenical administration form together with suitable, non-toxic, inert, therapeutically compatible solid or liquid carrier materials and, if desired, the usual pharmaceutical adjuvants.

As carrier materials, there are suitable not only inorganic carrier materials, but also organic carrier materials. Thus, for tablets, coated tablets, dragees and hard gelatine capsules there can be used as carrier materials, for example, lactose, maize starch or derivatives thereof, talc, stearic acid or its salts. Suitable carriers for soft gelatine capsules are, for example, vegetable oils, waxes, fats and semi-solid and liquid polyols (depending on the nature of the active substance no carriers are, however, required in the case of soft gelatine capsules). Suitable carrier materials for the preparation of solutions and syrups are, for example, water, polyols, saccharose, invert sugar and glucose. Suitable carrier materials for injection solutions are, for example, water, alcohols, polyols, glycerine and vegetable oils. Suitable carrier materials for suppositories are, for example, natural or hardened oils, waxes, fats and semi-liquid or liquid polyols.

As pharmaceutical adjuvants there come into consideration the usual stabilizing, preserving, wetting and emulsifying agents, flavor-improving agents, salts for varying the osmotic pressure, buffer substances, solubilizers, coloring and coating agents and antioxidants.

The dosage of the compounds of formula III can vary within wide limits depending on the illness to be treated, the age and the individual condition of the patient and on the mode of administration and is, of course, adjusted to the individual requirements in each particular case. For the prophylaxis and therapy of infectious diseases which are caused by bacteria, fungi or parasites, there comes into consideration for adult patients a daily dosage of about 0.01 g to about 4 g, especially about 0.05 g to about 2 g. Depending on the dosage, it is convenient to administer the daily dosage in several unit dosages.

The pharmaceutical preparations conveniently contain about 10-1000 mg, preferably 50-500 mg, of a compound of formula III.

The following Examples serve to illustrate further the invention in more detail. All temperatures are given in degrees Celsius.

EXAMPLE 1

(i) 0.22 g of 1,3-diamino-2-methylimidazolium chloride are dissolved in 5 ml of glacial acetic acid, whereupon the solution is treated with a solution of 0.45 g of 4-dimethylaminobenzaldehyde in 5 ml of glacial acetic acid. After stirring for 2 hours the yellow precipitate is removed by filtration. After drying, there is obtained 1,3-bis[[p-(dimethylamino)benzylidene]amino]-2-methylimidazolium chloride of decomposition point 264°-266°. The mother liquor is treated with ether, whereby a second portion of the desired product is obtained. The material obtained is recrystallized from hot water. There is obtained 1,3-bis[[p-(dimethylamino)benzylidene]amino]-2-methylimidazolium chloride of decomposition point 270°.

(ii) 2.02 g of 1,3-diamino-imidazolium chloride and 4.5 g of 4-dimethylaminobenzaldehyde are dissolved at 50° in 100 ml of glacial acetic acid, whereupon the solution is stirred at room temperature for 15 hours. Yellow crystals result. One hundred (100) ml of ether are added thereto. The mixture is suction filtered while washing with 100 ml of ether and the material obtained is dried at 60°. By recrystallization from 250 ml of ethanol, there is obtained 1,3-bis-[[(p-dimethylamino)benzylidene]amino]imidazolium chloride of melting point 244°.

(a) 3.28 g of 1,3-bis[[p-dimethylamino)-benzylidene]amino]-2-methylimidazolium chloride are suspended in 200 ml of chloroform and 400 ml of saturated sodium hydrogen carbonate solution and stirred at room temperature for 18 hours. The product is filtered and washed with water. There is obtained 1,3-bis[[p-(dimethylamino)benzylidene]amino]-2-methylimidazolium hydrogen carbonate of melting point 144°-146° (dec.).

In an analogous manner:

(b) From 1,3-bis[[(p-dimethylamino)benzylidene]amino]imidazolium chloride, there is obtained 1,3-bis[[p-(dimethylamino)benzylidene]amino]imidazolium hydrogen carbonate of melting point 103°-104° (dec.).

EXAMPLE 2

(i) 1.49 g of 4-dimethylamino-benzaldehyde are added to a solution of 0.88 g of 1,3-diamino-2-isopropylimidazolium chloride in 15 ml of glacial acetic acid. After allowing the reaction mixture to stand at room temperature for 2 days, the product is crystallized out by the addition of ether and then recrystallized from ethanol. There is obtained 1,3-bis[[p-(dimethylamino)benzylidene]amino]-2-isopropyl-imidazolium chloride of melting point 241°.

(ii.a) 2.16 g of 3,4,5-trimethoxybenzyl chloride are added to a solution of 1.99 g of 1-benzylideneamino-2-ethylimidazole in 10 ml of acetonitrile and the mixture is heated under reflux for 28 hours. The crystallized-out product is filtered and washed with ether. There is obtained 1-benzylideneamino-2-ethyl-3-(3,4,5-trimethoxybenzyl)imidazolium chloride of melting point 205°.

(ii.b) 3.1 g of 1-benzylideneamino-2-ethyl-3-(3,4,5-trimethoxybenzyl)imidazolium chloride are dissolved in 70 ml of water, whereupon the solution is treated with 8 ml of 25 percent hydrochloric acid. The resulting benzaldehyde is removed by steam distillation. After evaporation, the product is recrystallized from ethanol/ether. There is obtained 1-amino-2-ethyl-3-(3,4,5-trimethoxy-benzyl)imidazolium chloride of melting point 174°.

(ii.c) 1.9 g of 1-amino-2-ethyl-3-(3,4,5-trimethoxybenzyl)imidazolium chloride are dissolved in 38 ml of glacial acetic acid, whereupon the solution is treated with 0.86 g of p-dimethylaminobenzaldehyde and stirred at room temperature for 52 hours and the solution is evaporated. The product is recrystallized from ethanol/ether. There is obtained 2-ethyl-1-[[p-(dimethylamino)benzylidene)amino]-3-(3,4,5-trimethoxybenzyl)imidazolium chloride of melting point 211°.

(iii) A solution of 2.42 g of 1-[[p-(dimethylamino)benzylidene]amino]-2-ethylimidazole is treated with 2.42 g of p-dimethylaminophenacyl bromide. After stirring at 40° for 30 minutes, the product is crystallized out by the addition of ether and recrystallized from methylene chloride/ether. There is obtained 3-[p-dimethylamino)phenacyl]-1-[[p-(dimethylamino)benzylidene]amino]-2-ethylimidazolium bromide of melting point 247°.

(a) 3.0 g of 1,3-bis[[p-(dimethylamino)benzylidene]amino]-2-isopropylimidazolium chloride are suspended in 200 ml of saturated sodium hydrogen carbonate solution and stirred at room temperature for 18 hours. The product is filtered and washed firstly with water and then with ether. There is obtained 1,3-bis[[p-(dimethylamino)benzylidene]amino]-2-isopropylimidazolium hydrogen carbonate of melting point 124°-126° (dec.).

In an analogous manner:

(b) From 2-ethyl-1-[[p-(dimethylamino)benzylidene]amino]-3-(3,4,5-trimethoxybenzyl)imidazolium chloride, there is obtained 2-ethyl-1-[[p-(dimethylamino)benzylidene]-3-(3,4,5-trimethoxybenzyl)imidazolium hydrogen carbonate of melting point 75° (dec.);

(c) from 3-[p-(dimethylamino)phenacyl]-1-[[p-(dimethylamino)benzylidene]amino]-2-ethylimidazolium bromide, there is obtained 3-[p-(dimethylamino)-phenacyl]-3-[[p-(dimethylamino)benzylidene]amino]-2-ethylimidazolium hydrogen carbonate of melting point 122° (dec.).

EXAMPLE 3

(a) 1.3 g of 1,3-bis[[p-(dimethylamino)benzylidene]amino]-2-isopropylimidazolium hydrogen carbonate are dissolved in 10 ml of methanol and 2 ml of glacial acetic acid are added thereto. After stirring at room temperature for 16 hours, the solution is concentrated and the product is crystallized by the addition of ether. After two-fold recrystallization from methanol/ether, there is obtained 1,3-bis[[p-(dimethylamino)benzylidene]amino]2-isopropylimidazolium acetate of melting point 150°-151°.

In an analogous manner:

(b) From 1,3-bis[[p-(dimethylamino)benzylidene]amino]-2-methylimidazolium hydrogen carbonate, there is obtained 1,3-bis[[p-(dimethylamino)- benzylidene]amino]-2-methylimidazolium acetate of melting point 159°14 162°.

EXAMPLE 4

(a) 48 mg of 1,3-bis[[p-(dimethylamino)benzylidene]amino]-2-isopropylimidazolium hydrogen carbonate are dissolved in 4 ml of methanol and 9.6 mg of methanesulfonic acid are added thereto. After 10 minutes, the solution is concentrated at room temperature in a vacuum and the product is crystallized by the addition of ether. There is obtained 1,3-bis[[p-(dimethylamino)benzylidene]amino]-2-isopropylimidazolium methanesulfonate of melting point 238°–239°.

In an analogous manner:

(b) From 1,3-bis[[p-(dimethylamino)benzylidene]amino]-2-methylimidazolium hydrogen carbonate, there is obtained 1,3-bis[[p-(dimethylamino)benzylidene]amino]-2-methylimidazolium methanesulfonate of melting point 255°–257° (dec.).

EXAMPLE 5

25 mg of 1,3-bis[[p-(dimethylamino)benzylidene]amino]-2-isopropylimidazolium acetate are suspended in 5 ml of saturated sodium hydrogen carbonate solution. After stirring for three days the product is filtered and washed with water. There is obtained 1,3-bis[[p-(dimethylamino)benzylidene]amino]-2-isopropylimidazolium hydrogen carbonate of melting point 122°–124°.

EXAMPLE 6

100 mg of 1,3-bis[[p-(dimethylamino)benzylidene]amino]-2-isopropylimidazolium hydrogen carbonate are suspended in 3 ml of water and 2 ml of 10 percent hydrogen bromide solution are added thereto. After 15 minutes the product is filtered, washed with water and recrystallized from ethanol. There is obtained 1,3-bis[[p-(dimethylamino)benzylidene]amino]-2-isopropylimidazolium bromide of melting point 241° (dec.).

EXAMPLE 7

(i) 2.05 g of 1,3-bis[[p-(dimethylamino)benzylidene]amino]-2methylimidazolium chloride and 7.35 g of N,N-dimethylformamide diethyl acetal are stirred at 100° for 45 minutes in 150 ml of 1-propanol. The product is precipitated by the addition of ether. It is crystallized from dichloromethane/methanol and recrystallized from ethanol. There is obtained 1,3-bis[[p-(dimethylamino)benzylidene]amino]-2-[2-(dimethylamino)vinyl]imidazolium chloride of melting point 246°–248°.

(a) 2.75 g of 1,3-bis[[p-(dimethylamino)benzylene]-2-[2-(dimethylamino)vinyl]imidazolium chloride are suspended in 100 ml of saturated sodium hydrogen carbonate solution and stirred at room for 16 hours. The product is filtered and washed with water. There is obtained 1,3-bis[[p-(dimethylamino)benzylidene]amino]-2-[2-(dimethylamino)vinyl-]imidazolium hydrogen carbonate of melting point 160°–161°.

EXAMPLE 8

1.0 g of 1,3-bis[[p-(dimethylamino)benzylidene]amino]-2-[2-(dimethylamino)vinyl-]imidazolium hydrogen carbonate is dissolved in 20 ml of methanol and 3 ml of glacial acetic acid. After 20 minutes, the solution is concentrated at room temperature in a vacuum. The product is crystallized by the addition of ether and recrystallized three times from methanol/ether. There is obtained 1,3-bis[[p-(dimethylamino)benzylidene]amino]-2-[2-dimethylamino)-vinyl]imidazolium acetate of melting point 182° (dec.).

EXAMPLE 9

(i.a) 32.8 g of sodium hydride (55 percent dispersion in oil) are washed with absolute tetrahydrofuran. A solution of 53.1 g of 2-phenylimidazole in 1500 ml of N-methylpyrrolidone is then added dropwise thereto at 0°. The mixture is stirred at 0° for a half hour and at room temperature for about 1.5 hours (until gas evolution is no longer to be observed). 85 g of O-diphenylphosphinylhydroxylamine are now added thereto. The mixture is stirred at room temperature for 20 hours and subsequently 910 ml of water are added thereto. The dark solution is stirred at room temperature for 1 hour and then extracted seven times with 300 ml of dichloromethane each time. The extract is dried over sodium sulfate and evaporated. The residual oil is placed on a column loaded with 900 g of silica gel, whereupon the 1-amino-2-phenylimidazole is eluted with dichloromethane/ethanol (85:15).

(i.b) 43.8 g of O-diphenylphosphinylhydroxylamine are added to 30.1 g of 1-amino-2-phenylimidazole in 2000 ml of dichloromethane. After stirring at room temperature for 3 days an additional 21.9 g of O-diphenylphosphinylhydroxylamine are added. After one day, the mixture is filtered and the filter material is washed four times with 150 ml of dichloromethane each time. The residue is placed on a column loaded with 700 ml of ion-exchanger Amberlite IRA 400 (chloride), whereupon elution is carried out with water. The eluate is evaporated and the residue is treated with ethanol and evaporated. After drying in a high vacuum over potassium hydroxide, there is obtained 1,3-diamino-2-phenylimidazolium chloride.

(i.c) 0.45 g of 1,3-diamino-2-phenylimidazolium chloride are dissolved in 6 ml of glacial acetic acid and 0.64 g of 4-dimethylaminobenzaldehyde are added. After stirring for 24 hours, about 1 ml of absolute ether is added. One day later, the mixture is evaporated and the residue is placed on a column loaded with 25 g of silica gel. After elution with dichloromethane/ethanol (98:2) and crystallization from ethanol/ether, there is obtained 1,3-bis[[p-(dimethylamino)benzylidene]amino]-2-phenylimidazolium chloride of melting point 242°.

(a) 95 mg of 1,3-bis[[p-(dimethylamino)benzylidene]amino]-2-phenylimidazolium chloride are suspended in 10 ml of saturated sodium hydrogen carbonate solution and the suspension is stirred at room temperature for 18 hours. The product (1,3-bis[[p-(dimethylamino)benzylidene]amino]-2-phenylimidazolium hydrogen carbonate) is filtered, washed with water and ether. The still moist product is subsequently dissolved in 10 ml of methanol and treated with 2 ml of glacial acetic acid. The solution is evaporated at room temperature in a vacuum and the residue is crystallized from methanol/ether. There is obtained 1,3-bis[[p-(dimethylamino)benzylidene]amino]-2-phenyl imidazolium acetate of melting point 167°.

EXAMPLE A 1,3-Bis[[(p-dimethylamino)benzylidene]amino]-2-[2-(dimethylamino)vinyl]imidazolium acetate is used in a manner known as the active substance for the preparation of tablets of the following composition:

|  | mg/tablet |
|---|---|
| Active substance of formula III | 100 |
| Lactose | 192 |
| Maize starch | 80 |
| Hydrolyzed maize starch | 20 |
| Calcium stearate | 8 |
| Tablet weight | 400 mg |

The compounds listed hereinafter can also be used as active substances:

1,3-Bis[[(p-dimethylamino)benzylidene]amino]-2-phenylimidazolium acetate;

1,3-bis[[(p-dimethylamino)benzylidene]amino]-2-isopropylimidazolium acetate;

1,3-bis[[(p-dimethylamino)benzylidene]amino]-2-isopropylimidazolium methanesulfonate;

1,3-bis[[(p-dimethylamino)benzylidene]amino]-2-methylimidazolium acetate and 1,3-bis[[p-(dimethylamino)benzylidene]amino]-2-methylimidazolium methanesulfonate.

I claim:

1. A compound of the formula

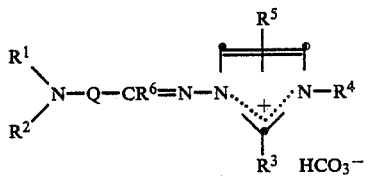

I wherein the symbol Q is unsubstituted phenylene or naphthylene, or phenylene or naphthylene substituted by one or two substituents selected form the group consisting of lower alkyl, lower alkoxy, lower alkylthio, lower alkanoyl, lower alkoxycarbonyl, phenyl, halogen, trifluoromethyl, hydroxy, nitro and cyano, $R^1$ and $R^2$, independently, are hydrogen or lower alkyl, $R^3$ is hydrogen, lower alkyl, lower hydroxyalkyl, lower alkoxyalkyl, lower haloalkyl, lower alkylthio, lower alkoxy or the group $-(A)_n-Ra$, $R^4$ is a saturated or partially unsaturated lower hydrocarbon group, a group of the formula $-NRR'$ wherein R and R', independently, are hydrogen or lower alkyl, or the group $-N=CRc-Rb$, $-CHRcRd$, $-NH-CHRcRd$, $-NH-CO-Re$ or $-CHRc-Co-Re$, $R^5$ is hydrogen, lower alkyl, lower hydroxyalkyl, lower alkoxyalkyl, lower haloalkyl, unsubstituted phenyl or naphthyl, or phenyl or naphthyl substituted by one, two or three substituents selected form the group consisting of lower alkylamino, di(lower alkyl)-amino, lower alkyl, lower alkoxy, lower alkylthio, lower alkanoyl, lower alkoxycarbonyl, phenyl, halogen, trifluoromethyl, hydroxy, nitro and cyano, $R^6$ is hydrogen or lower alkyl, Ra and Rb each are unsubstituted phenyl or naphthyl, or phenyl or naphthyl substituted by one, two or three substituents selected form the group consisting of lower alkylamino, di(lower alkyl)amino, lower alkyl, lower alkoxy, lower alkylthio, lower alkanoyl, lower alkoxycarbonyl, phenyl, halogen, trifluoromethyl, hydroxy, nitro and cyano, or a group of the formula $-NRR'$ wherein R and R', independently, are hydrogen or lower alkyl, Rc is hydrogen or lower alkyl, Rd is unsubstituted phenyl or naphthyl, or phenyl or naphthyl substituted by one, two or three substituents selected form the group consisting of lower alkylamino, di(lower alkyl)amino, lower alkyl, lower alkoxy, lower alkylthio, lower alkanoyl, lower alkoxycarbonyl, phenyl, halogen, trifluoromethyl, hydroxy, nitro and cyano, Re is hydrogen, a saturated or partially unsaturated lower hydrocarbon group optionally attached via an oxygen atom or unsubstituted phenyl or naphthyl, or phenyl or naphthyl substituted by one, two or three substituents selected form the group consisting of lower alkyamino, di(lower alkyl)amino, lower alkyl, lower alkoxy, lower alkylthio, lower alkanoyl, lower alkoxycarbonyl, phenyl, halogen, trifluoromethyl, hydroxy, nitro and cyano, or a group of the formula $-NRR'$ wherein R and R', independently, are hydrogen or lower alkyl, A is vinylidene or lower alkylene, n is the number 0 or 1 and the dotted line is an additional double bond.

2. A compound, in accordance with claim 1, wherein $R^3$ is lower alkyl.

3. A compound, in accordance with claim 1, wherein $R^3$ is the group $-(A)_n-Ra$.

4. A compound, in accordance with claim 3, wherein n is 0 and Ra is unsubstituted phenyl or phenyl substituted by one, two or three substituents from the group consisting of lower alkyl, lower alkoxy, lower alkylthio, halogen, nitro and di(lower alkyl)amino.

5. A compound, in accordance with claim 4, wherein Ra is unsubstituted phenyl or phenyl mono-substituted by lower alkyl, lower alkoxy or halogen.

6. A compound, in accordance with claim 5, wherein $R^5$ is hydrogen.

7. A compound, in accordance with claim 5, wherein $R^4$ is the group $-N=CR^6-Q-NR^1R^2$.

8. A compound, in accordance with claim 5, wherein $R^4$ is the group $-N=CRc-Rb$.

9. A compound, in accordance with claim 8, wherein Rc is hydrogen.

10. A compound, in accordance with claim 9, wherein Rb is unsubstituted phenyl or phenyl substituted by one, two or three substituents from the group consisting of lower alkyl, lower alkoxy, lower alkylthio, halogen and nitro.

11. A compound, in accordance with claim 10, wherein Q is 1,4-phenylene which can be substituted by one or two substituents from the group consisting of lower alkyl and lower alkoxy.

12. A compound, in accordance with claim 11, wherein Q is 1,4-phenylene.

13. A compound, in accordance with claim 12, wherein $R^1$ and $R^2$ each are lower alkyl.

14. A compound, in accordance with claim 13, wherein $R^6$ is hydrogen.

15. A compound in accordance with claim 3, wherein n is 1, A is vinylene, Ra is the group $-NRR'$ and R and R' each are hydrogen or lower alkyl.

16. A compound, in accordance with claim 15, wherein R and R' each are lower alkyl.

17. A compound, in accordance with claim 15, wherein $R^5$ is hydrogen.

18. A compound, in accordance with claim 15, wherein $R^4$ is the group $-N=CR^6-Q-NR^1R^2$.

19. A compound, in accordance with claim 15, wherein $R^4$ is the group $-N=CRc-Rb$.

20. A compound, in accordance with claim 19, wherein Rc is hydrogen.

21. A compound, in accordance with claim 20, wherein Rv is unsubstituted phenyl or phenyl substituted by one, two or three substituents from the group consisting of lower alkyl, lower alkoxy, lower alkylthio, halogen and nitro.

22. A compound, in accordance with claim 21, wherein Q is 1,4-phenylene which can be substituted by one or two substituents from the group consisting of lower alkyl and lower alkoxy.

23. A compound, in accordance with claim 22, wherein Q is 1,4-phenylene.

24. A compound, in accordance with claim 23, wherein $R^1$ and $R^2$ each are lower alkyl.

25. A compound, in accordance with claim 24, wherein $R^6$ is hydrogen.

26. A compound, in accordance with claim 1, 1,3-Bis[[p-(dimethylamino)benzylidene]amino]-2-[2-(dimethylamino)vinyl]imidazolium hydrogen carbonate.

27. A compound, in accordance with claim 1, 1,3-Bis[[p-(dimethylamino)benzylidene]amino]-2-isopropylimidazolium hydrogen carbonate.

28. A compound in accordance with claim 1, 1,3-Bis-[[p-(dimethylamino)benzylidene]amino]-2-methylimidazolium hydrogen carbonate.

29. A compound, in accordance with claim 1, 1,3-Bis[[p-(dimethylamino)benzylidene]amino]-2-phenylimidazolium hydrogen carbonate.

* * * * *

UNITED STATES PATENT AND TRADEMARK OFFICE
CERTIFICATE OF CORRECTION

PATENT NO. : 4,808,727

DATED : February 28, 1989

INVENTOR(S) : Helmut Link

It is certified that error appears in the above-identified patent and that said Letters Patent is hereby corrected as shown below:

In claim 1, column 24, line 24, "vinylidene" should be --vinylene--;

and

In claim 21, column 25, line 8, "Rv" should be -- Rb --.

Signed and Sealed this

Fourteenth Day of November, 1989

*Attest:*

JEFFREY M. SAMUELS

*Attesting Officer*     *Acting Commissioner of Patents and Trademarks*